United States Patent [19]

Brownlee et al.

[11] 4,134,408

[45] Jan. 16, 1979

[54] CARDIAC PACER ENERGY CONSERVATION SYSTEM

[75] Inventors: Robert R. Brownlee, State College; Frank O. Tyers, Hershey, both of Pa.

[73] Assignee: Research Corporation, New York, N.Y.

[21] Appl. No.: 741,491

[22] Filed: Nov. 12, 1976

[51] Int. Cl.² ............................................. A61N 1/36
[52] U.S. Cl. ............................................. 128/419 PS
[58] Field of Search ................... 128/419 PG, 419 PS, 128/421, 422

[56] References Cited

U.S. PATENT DOCUMENTS

| | | | |
|---|---|---|---|
| 3,195,540 | 7/1965 | Waller | 128/419 PG |
| 3,311,111 | 3/1967 | Bowers | 128/419 PG |
| 3,783,877 | 1/1974 | Bowers | 128/419 PS |
| 3,835,864 | 9/1974 | Rasor et al. | 128/419 PG X |
| 3,968,802 | 7/1976 | Ballis et al. | 128/419 PG |

FOREIGN PATENT DOCUMENTS 1425107  2/1976  United Kingdom .............. 128/419 PS

OTHER PUBLICATIONS

Senning, "Journal of Thoracic and Cardiovascular Surgery", vol. 38, No. 5, Nov. 1959, p. 639.

Primary Examiner—William E. Kamm
Attorney, Agent, or Firm—Cooper, Dunham, Clark, Griffin & Moran

[57] ABSTRACT

A system for extending the lifetime of an implantable cardiac pacer of the type having an internal primary battery power source includes an external energy transmitting source for selectively externally powering the pacer in order to reduce consumption of the internal battery power. While the pacer is operating on external power, current drain from the internal primary battery is reduced substantially to zero, thus extending useful battery life. The external energy source may include an electromagnetic energy transmitting coil, which transmits energy to an implanted energy receiving coil, the received energy being then rectified, filtered, and used to power the pacer. If a large-diameter energy transmitting coil is employed, the transmitting and receiving coils may be loosely coupled to provide a more convenient and easy-to-use energy conservation system. Alternatively, the external energy source may comprise a radio-frequency source, and transmitted radio-frequency energy may be received by an internal antenna which may comprise the cardiac pacing lead electrode system. The energy conservation system may also be provided with a secondary or rechargeable battery of lower energy capacity than that of the primary battery, which secondary battery may be repeatedly recharged from the external energy source to further extend the life of the primary source. In order to stabilize and reduce system current drain, a series-type voltage regulator may be provided between the primary battery and the pacer circuitry.

7 Claims, 9 Drawing Figures

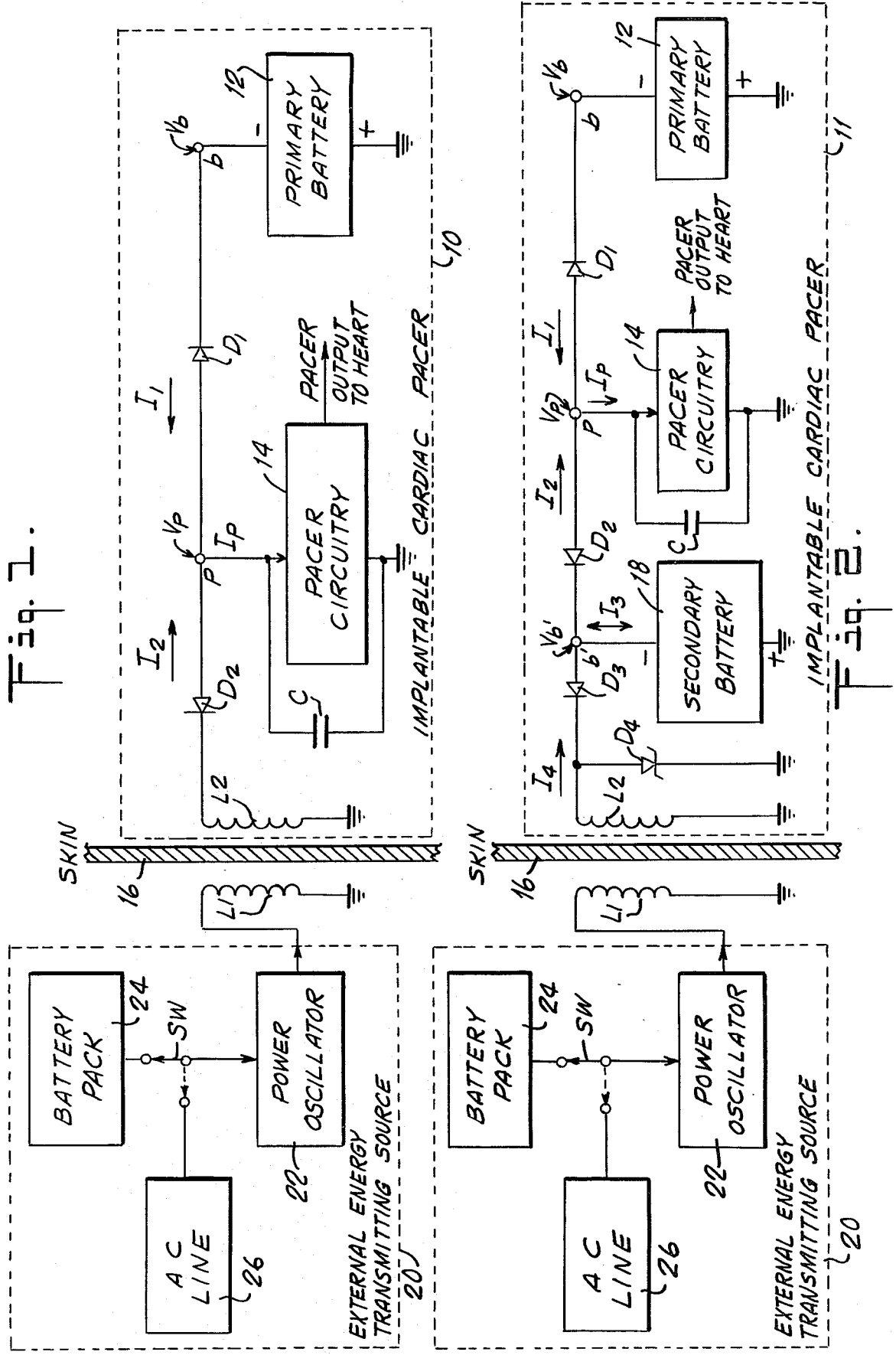

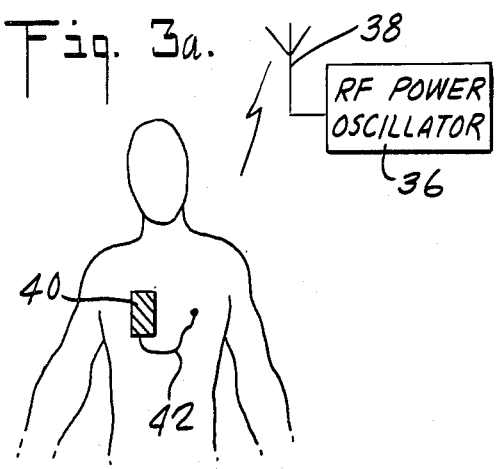
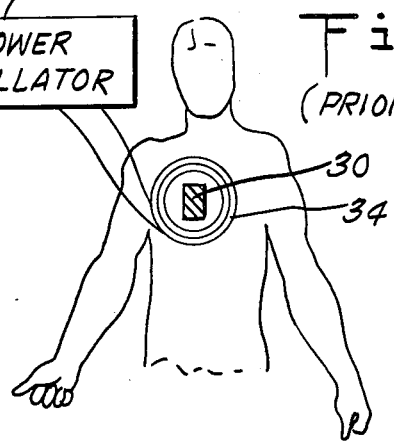
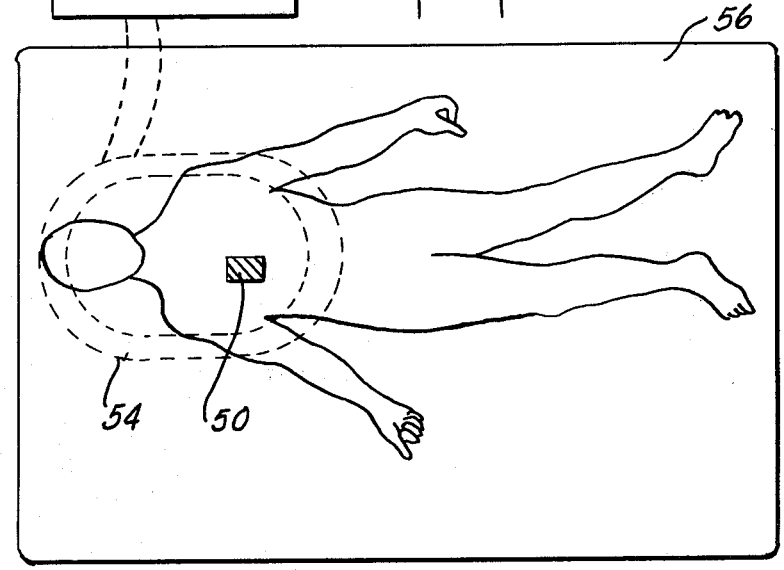
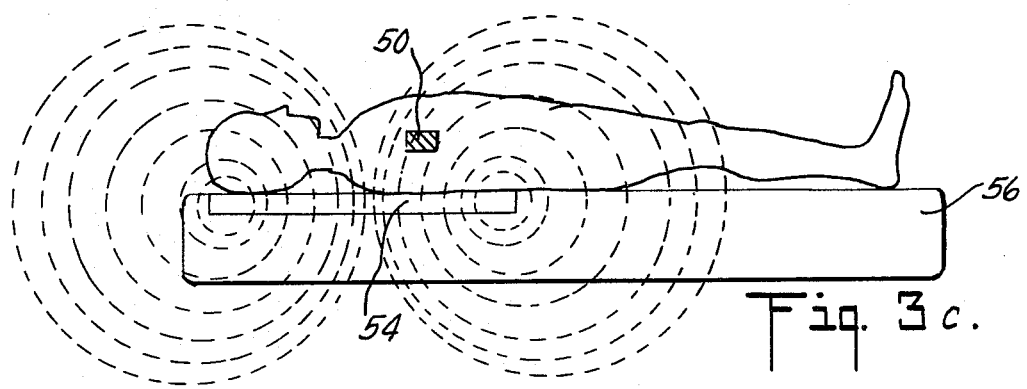

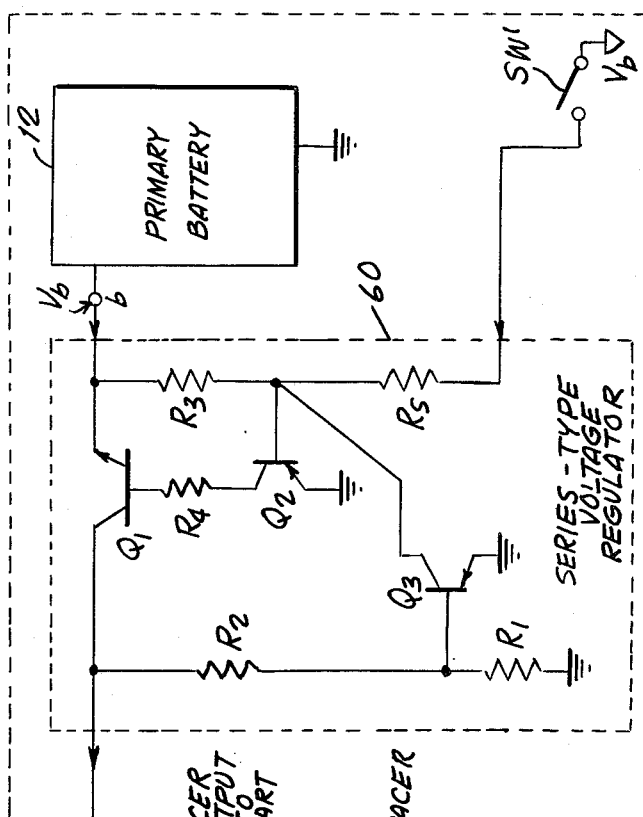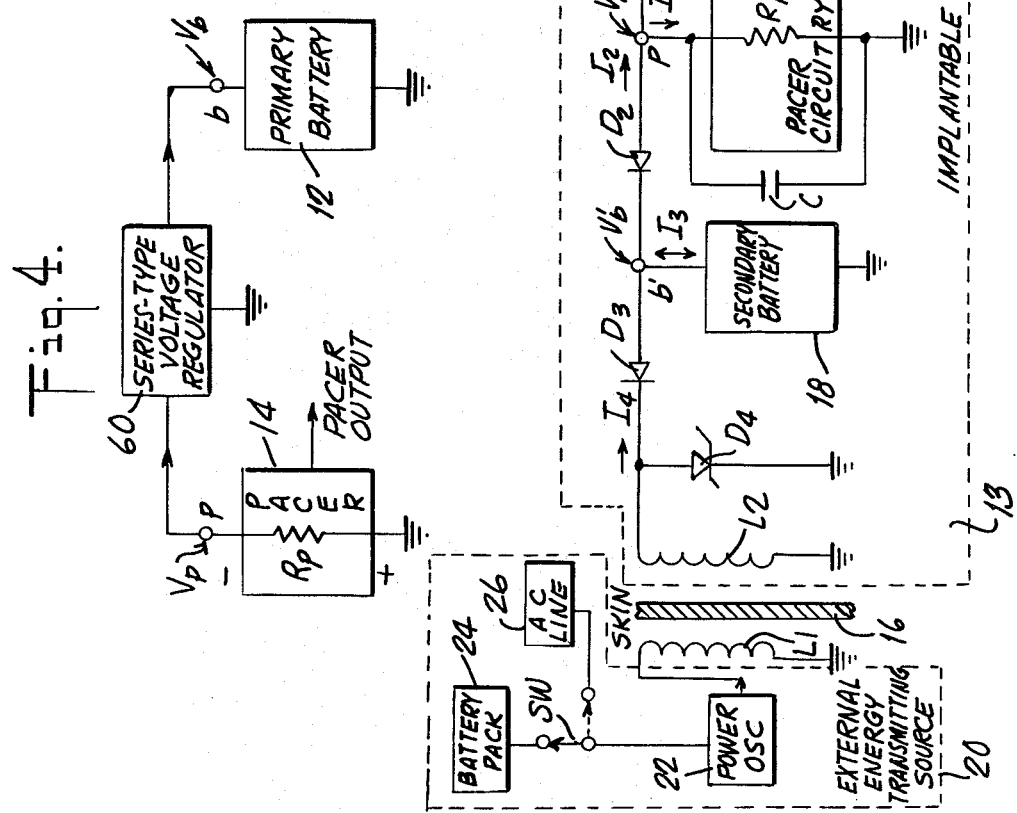

CARDIAC PACER ENERGY CONSERVATION SYSTEM

BACKGROUND OF THE INVENTION

This invention relates to cardiac pacers, and is specifically directed to an energy conservation system for extending the useful lifetime of an implantable cardiac pacer of the type having an internal primary battery power source.

It has long been recognized that an electronic circuit implanted within the human body may be powered by an external power source, as representatively shown in U.S. Pat. No. 3,727,616. Similarly, many conventional, nonimplanted electronic circuits may be switchably powered either by an internal battery or from an external AC source, as illustrated in British Pat. No. 826,766.

Implantable devices having a plurality of batteries in combination with isolation diodes are shown in U.S. Pat. Nos. 3,738,371 and 3,783,877, while the use of a regulated power supply to power only a portion of a cardiac pacer is shown in U.S. Pat. No. 3,547,127. However, none of the power supply configurations disclosed in the aforementioned references show or suggest an energy conservation system for extending the lifetime of an implantable cardiac pacer having an internal primary battery power source.

Within the past few years, new types of primary batteries have received considerable attention for use in cardiac pacers, primarily because of their potential for enhancing the useful lifetime of such pacers. Principal among the new primary cells employed is the solid-state lithium-iodine chemical cell or lithium battery, which, when used in conjunction with low-current pacer circuitry, can result in a useful battery lifetime in the order of several years. However, the lithium battery possesses a number of features which have heretofore limited its application in cardiac pacers. It exhibits an open-circuit voltage in the order of 2.8 volts, or about twice that of conventional cells, and has an internal resistance which increases throughout the lifetime of the cell. This increasing internal resistance causes a substantial and undesirable drop in output voltage under load. Furthermore, as the lithium battery is a primary cell, it is nonrechargeable, and its energy density is not adequate for constructing small cardiac pacers with useful lifetimes in the range of ten or more years. For these reasons, a substantial need has heretofore existed for energy conservation means for extending the lifetime of an implantable cardiac pacer powered by a primary source such as the lithium battery.

SUMMARY OF THE INVENTION

An object of the invention is to provide an energy conservation system for extending the useful lifetime of an implantable cardiac pacer of the type having an internal primary battery power source.

It is a further object of the invention to provide an energy conservation system which is particularly adapted to the characteristics of the lithium battery, although the invention is not limited to this application.

In accordance with the invention, an implantable pacer of the type having an internal primary battery power source is provided with energy receiving means for detecting electromagnetic energy transmitted from an external energy source. When the external energy source is activated, electromagnetic energy is detected by the energy receiving means and is suitably processed to provide a DC supply voltage to the pacer circuitry. While the implanted pacer is being operated from energy received from the external source, current drain from the internal primary battery is reduced substantially to zero, thus extending useful battery life.

In one embodiment of the invention, the external energy source may include an electromagnetic energy transmitting coil, which transmits energy to a companion energy receiving coil implanted within the patient. A particularly convenient and easy-to-use system is achieved by providing a large-diameter energy transmitting coil, which may be loosely coupled to the receiving coil and still induce sufficient energy to power the implanted pacer. This feature permits the use of a variety of convenient coupling configurations. For example, the large-diameter transmitting coil may be mounted within the patient's bed or arm chair, with the energy transmitting apparatus automatically pressure-activated, so that the patient's cardiac pacer will automatically be powered externally whenever the patient is in bed or sitting in a chair.

In an alternative embodiment of the invention, the external energy-transmitting source may operate at radio frequencies, with the radio-frequency energy being received by an implanted antenna. In order to simplify the lead electrode-pacer interface, the antenna may comprise the cardiac pacer electrode structure.

In order to further enhance the energy conservation capabilities of the present invention, a small secondary or rechargeable battery may be provided within the implantable portion of the system. The purpose of this small rechargeable battery is to permit the pacer to operate on internal power for a few days without drawing any current from the primary battery. Thus, if the patient is temporarily unable to utilize the external energy transmitter, or if the transmitter is disabled, the primary cell will not immediately be subject to loading.

The useful lifetime of the primary pacer battery in the present invention may be further extended by providing a series-type voltage regulator between the primary battery source and the cardiac pacer circuitry. This configuration is particularly advantageous when a lithium primary battery is employed, due to the unique characteristics of the lithium battery. Although the lithium battery provides a relatively high initial voltage of about 2.8 volts, battery impedance increases very substantially as the cell is depleted, so that output voltage under load near the end of battery life may be in the range of only about 1.5 volts. Accordingly, previous pacer circuits employing lithium batteries have been designed to operate properly at about 1.5 volts. Although such circuits function properly at the substantially higher initial battery voltage, current drain at the higher voltage is almost twice that necessary to maintain proper circuit operation. By providing a series-type voltage regulator between the primary battery and the pacer circuitry, this problem can be substantially eliminated, since the pacer circuitry can be provided with a constant desired voltage, typically in the range of about 1.5 volts, thus stabilizing current drain throughout the useful life of the battery. This results in a substantial saving in energy consumption, even when the small additional current drawn by the voltage regulator circuitry is taken into account.

The invention will be more completely understood with reference to the following detailed description, to be read in conjunction with the accompanying drawings.

BRIEF DESCRIPTION OF THE DRAWINGS

FIG. 1 is a block diagram of an apparatus for selectively externally powering an implantable cardiac pacer in accordance with the invention;

FIG. 2 is an alternate embodiment of an apparatus for selectively externally powering an implantable cardiac pacer;

FIG. 3 shows an example of the conventional external powering arrangement.

FIGS. 3a, 3b and 3c are simplified illustrations of electromagnetic energy transmitting systems for selectively externally powering an implantable cardiac pacer in accordance with the invention;

FIG. 4 is a block diagram of an apparatus for extending the life of an implantable cardiac pacemaker;

FIG. 4a is a graph showing battery and pacer voltages as a function of time; and FIG. 5 is a schematic circuit diagram of an apparatus for selectively externally powering an implantable cardiac pacemaker.

DETAILED DESCRIPTION

Referring to FIG. 1 of the drawings, there is shown an apparatus for selectively externally powering an implantable cardiac pacer 10 having a primary battery 12 with an output terminal b which is coupled to pacer circuitry 14 through a diode $D_1$. Additionally, an energy receiving coil L2 is coupled to the pacer circuitry through a diode $D_2$. At junction point p between the anodes of diodes $D_1$ and $D_2$ the power supply input terminal of pacer circuitry 14 is connected to the energy-supplying system, which provides operating current $I_p$ to the pacer circuitry. A smoothing and filter capacitor C is connected across the power input terminals of the pacer circuitry, from p to ground. The aforementioned components comprise the implantable portion of the system, as shown to the right of skin surface 16 in FIG. 1.

Spaced apart from the implanted unit, and outside the skin surface, is the external energy transmitting source 20, which comprises a power oscillator 22 which may be selectively powered by either a battery pack 24 or by an AC line source 26, as determined by the setting of a power switch SW. The power oscillator and power supply portions of the external energy transmitting source 20 may be of any suitable configuration, and accordingly are not described in detail. The power oscillator may be set to operate at a suitable frequency for efficient coupling of electromagnetic energy, typically in the range of 1 KHz to 20 KHz. Higher frequencies may be usefully employed for nonmetallic encased implants.

The output of the external energy transmitting source, from power oscillator 22, is connected to an energy transmitting coil L1, which serves to transmit electromagnetic energy from the external energy source through the intervening air space and skin layer to the energy receiving coil L2 mounted within the implanted cardiac pacer 10.

When a patient, having a cardiac pacer in accordance with the invention implanted within his chest cavity, is not suitably positioned to receive energy from the external energy transmitting source 20, or when the external source is not activated, the pacer 10 is battery powered in a conventional manner. The primary battery 12 output voltage $V_b$ supplies current $I_1$ to the pacer circuitry 14 through diode $D_1$, and capacitor C serves to filter out variations in pacer supply voltage during the pacer operating cycle.

When the internal energy receiving coil L2 is suitably coupled to energy transmitting coil L1, and power oscillator 22 of the external energy transmitting source 20 is activated, transmitted electromagnetic energy is received by coil L2. This received energy is rectified by diode $D_2$ and filtered and smoothed by capacitor C to provide a DC current $I_2$ to the pacer circuitry 14 when sufficient energy is detected by coil L2 to cause the DC voltage generated at junction p from the energy receiving coil L2 to exceed the voltage provided to junction p by primary battery 12. At this point, diode $D_1$ in the primary battery circuit will be reverse biased, thus causing current $I_1$ from the primary battery to the pacer circuitry to be reduced substantially to zero, and the entire pacer current drain $I_p$ to be provided by current $I_2$ from coil L2 through diode $D_2$. It has been found that less than 0.5 watts of transmitting power from oscillator 22 at a frequency of 1 to 5 KHz into coil L1 is sufficient to generate a suitably large voltage in coil L2 to reduce current $I_1$ to zero, even with a fairly loosely coupled system. Thus, even for moderate transmitting power levels, there is no need to precisely locate the energy transmitting coil. This is a substantial advantage when the entire system is to be controlled by the patient. When the energy received by coil L2 is insufficient to generate a voltage at p in excess of the value $V_p$ provided by the primary battery, diode $D_2$ is reverse biased and the pacer is powered in a conventional manner by the primary battery, as discussed above.

Since the present invention is not dependent upon any particular design or configuration for coils L1 or L2, or upon any particular operating frequency for power oscillator 22, these components and their operating parameters may be of any suitable configuration, as will be within the purview of those skilled in the art. However, it has been found that certain configurations of the energy transmitting and receiving portions of the invention may be particularly advantageous, and these configurations accordingly will be described in greater detail hereinafter.

In the system shown in FIG. 2, the basic pacer energy system shown in FIG. 1 has been modified to include within the implantable pacer block 11 a diode $D_3$, a secondary battery 18 and a Zener diode $D_4$. The diode $D_3$ is connected in series with diode $D_2$ between the ungrounded end of coil L2 and the cathode of diode $D_2$, with like polarity to that of diode $D_2$. At a junction b' between the cathode of diode $D_2$ and the anode of diode $D_3$ is connected the secondary or rechargeable battery 18, of substantially lower energy capacity than that of the primary battery 12. For example, whereas the primary battery 12 may typically have a capacity of about 1 to 3 Ah, the capacity of rechargeable battery 18 may typically be about 0.1 Ah or less. Furthermore, the fully-charged voltage $V_b'$ at junction b' of rechargeable battery 18 exceeds the no-load voltage $V_b$ at junction b of primary battery 12.

The negative terminal of secondary battery 18 is connected to the junction b', while its positive terminal is grounded, as shown in FIG. 2. The Zener diode $D_4$ is connected across coil L2 to limit its output voltage, and thereby prevent overcharging of the secondary battery. The remaining system components shown in FIG. 2 are the same as those of FIG. 1, and for clarity, corresponding components have been provided with like designations.

The basic purpose of rechargeable battery 18 is to permit the pacer circuitry to operate on internal power for a few days at a time without drawing any current from the primary battery 12. By charging the secondary battery 18 to its fully-charged voltage $V_b'$ (which exceeds the voltage $V_b$ of the primary battery) through diode $D_3$ whenever the external energy transmitting source 20 is activated and suitably positioned with respect to the implantable cardiac pacer 11, a so-called "first line" internal power source is provided. When the external transmitting source 20 is deactivated, the pacer will be powered from secondary battery 18, since this battery has been charged to a higher voltage than that of the primary battery 12. The output voltage $V_b'$ from the rechargeable battery provides sufficient voltage at junction p to reverse bias diode $D_1$ and thereby reduce the current drain $I_1$ from the primary battery substantially to zero. The pacer circuitry will be powered from the secondary battery so long as its voltage remains above that of the primary battery, typically a period of a few days. Thus, if a patient having an implanted pacer in accordance with the invention is unable to utilize the external energy transmitting source for any reason, the pacer will operate on secondary battery power for a few days and thus prevent immediate loading of the primary battery.

After a few days have elapsed without use of the external energy transmitter, the voltage of secondary battery 18 will drop below that of primary battery 12, and the pacer circuitry 14 will then be powered from the primary battery through diode $D_1$. When the pacer circuitry is being powered by primary battery 12, diode $D_2$ is reversed biased, and this prevents the secondary battery or coil L2 from loading the primary battery. When the pacer is subsequently again powered by the external source 20, the primary battery is returned to its no-load state, and current $I_4$ from receiving coil L2 splits at junction b' into a first component $I_3$, which serves to recharge secondary battery 18, and a second component $I_2$, which powers the pacer circuitry 14 through diode $D_2$. Using the system shown in FIG. 2, it is thus possible for a patient to be completely independent of the external energy transmitting source for days at a time without shortening the life of the primary battery.

Referring to FIG. 3 of the drawings, there is shown a typical prior art configuration for providing external power to an implanted cardiac pacer 30. A power oscillator 32 of any suitable type provides an electromagnetic output to a relatively small-diameter energy transmitting coil 34, which must be positioned relatively precisely over the implanted pacer 30 in order to induce sufficient electromagnetic energy into an energy receiving coil located within the pacer.

A simplified and improved energy transmitting system, which is less critical with respect to positioning than the prior art system of FIG. 3 is shown in FIGS. 3b and 3c. In this system, large diameter coil 54, which corresponds to the energy transmitting coil L1 of FIG. 1 or 2, is mounted, as for example, within a bed 56 and is loosely coupled to an energy receiving coil (such as L2 of FIGS. 1 and 2) within an implanted pacer 50 when the patient is in bed. The pacer 50 may advantageously have a configuration such as that shown by reference numerals 10 or 11 in FIG. 1 or 2. With the system shown in FIGS. 3b and 3c, energy may be supplied continuously for long periods of time, as for example while the patient is asleep, and thus the primary battery of the pacer, as shown at 12 in FIGS. 1 and 2, may be placed in the standby condition for a substantial period of time each day. Thus, the useful lifetime of the primary battery may be substantially extended, and, if a secondary battery 18, such as that shown in FIG. 2 is used, the secondary battery may be regularly recharged while the pacer is on external power.

Using a large-diameter energy transmitting coil mounted in the patient's bed, as shown in FIGS. 3b and 3c, it has been found that transmitting power levels for support and/or trickle charging fall in the range of from about 20 to 30 watts at a typical frequency of about 5 KHz. Of course, if a smaller coil is used and more precisely positioned, power levels of less than 0.5 watts may be found sufficient as previously noted. The energy transmitting system may either be manually switched on by the patient at bedtime and turned off upon arising, or else on automatic, pressure-sensitive switch may be provided within the bed, thus permitting the system to operate automatically.

An alternate system for energy transmission to an implanted pacer is shown in FIG. 3a. An RF power oscillator 36 is provided with an antenna 38 for transmitting RF energy. An implanted cardiac pacer 40 is provided with a pacing and sensing electrode 42, which electrode also serves as an antenna for receiving the transmitted RF energy. By the use of suitable decoupling circuits within the implanted pacer, the received RF energy may be detected and processed to provide DC power for the pacer circuitry. Thus, for example, the electrode 42 shown in FIG. 3a may be substituted for the energy receiving coil L2 in FIGS. 1 and 2. This system results in a simplified energy transmitting configuration, and one which is less critical with respect to positioning of the transmitting element than the prior art system of FIG. 3.

In the simplified block diagram of FIG. 4, a further increase in the useful lifetime of primary cell 12 is achieved by providing a series-type voltage regulator 60 between the primary cell and pacer circuitry 14. The voltage regulator is not provided primarily for the purpose of voltage regulation per se, but rather for the purpose of extending the useful lifetime of the primary cell. Since the primary cell 12 may advantageously be a lithium primary battery, and the useful output voltage under load of this type of battery may vary from an initial voltage of about 2.8 volts down to about 1.5 volts near the end of useful life, the pacer circuitry of an unregulated system must be designed to operate properly at the 1.5 volt level.

Since the output voltage of the primary cell will be substantially higher than this value over a large percentage of the useful life of the battery, the current drain at such higher voltages with an unregulated system is substantially greater than that necessary to maintain proper circuit operation. By providing a series-type voltage regulator between the primary battery and the pacer circuitry, this extra current drain can be substantially eliminated. Using the system shown in FIG. 4, the pacer circuitry can be provided with a constant desired voltage $V_p$, typically in the range of about 1.5 volts, and thus current drain can be stabilized throughout the useful life of the battery at a value just above that required for proper circuit operation. There results a substantial saving in energy consumption, even when the small additional current drawn by the voltage regulator circuitry is taken into account.

The effect of the series-type voltage regulator of FIG. 4 is shown graphically in FIG. 4a. The upper curve represents the output voltage $V_b$ of a typical primary lithium battery, which is also the pacer voltage $V_p$ in a system in which the primary cell is connected directly to the pacer circuitry. Since the pacer circuitry may be approximated for long-term power consumption calculations by a constant equivalent resistance $R_p$ of about 100,000 ohms, the initial current drain of the pacer circuitry at 2.8 volts will be nearly twice that of the regulated system, which provides a relatively constant output voltage $V_p$ of about 1.5 volts with the same battery, as shown in the substantially flatter lower curve $V_p$ of FIG. 4a. Due to this substantially higher current drain over a large portion of the useul lifetime of the battery, the battery in the prior art system is depleted much more rapidly than the battery of the regulated system, and so the output voltage $V_b$ drops below the minimum useful pacer voltage of just under 1.5 volts at a time $T_1$ which occurs substantially sooner than the equivalent voltage dropout point at a time $T_2$ for the regulated system. Clearly, the exact increase in useful operating life will depend upon many factors, such as battery characteristics, load impedance and efficiency of the regulator, but an improvement in useful life on the order of about 33% can be expected.

An implantable cardiac pacer having a series-type voltage regulator is shown in greater detail in the circuit diagram of FIG. 5. With the exception of the voltage regulator, indicated generally by the reference numeral 60, implantable cardiac pacer 13 of FIG. 5 is the same as pacer 11 of FIG. 2, and corresponding components have again been provided with like designations for clarity.

The series-type voltage regulator is inserted in the circuit between the primary battery 12 and the pacer circuitry 14. The input to the regulator comprises the unregulated output voltage $V_b$ of primary battery 12, and the regulator provides a regulated output voltage $V_p$ at p of about 1.5 volts to the pacer circuitry 14, as shown in FIG. 5. The circuit shown for voltage regulator 60 is a conventional 3-transistor low-current regulator design, although any suitable low-current series-type regulator circuit may be used. In the regulator circuit shown, transistor $Q_1$ serves as a series regulating element, which is controlled in a known manner by resistors $R_1$–$R_4$ and control transistors $Q_2$ and $Q_3$. A second input to the regulator circuit through switch SW' and resistor $R_5$ serves to bypass the regulator function by substantially saturating series regulator $Q_1$ through control transistor $Q_2$, thereby ensuring that the pacer circuitry voltage $V_p$ will increase to the primary battery voltage $V_b$ less only the small saturated collector-emitter voltage of transistor $Q_1$. By making switch SW' an externally activated magnetic switch, the internal voltage regulator 60 may be effectively bypassed in case of regulator malfunction, to provide maximum power supply voltage to generate higher amplitude pacer output pulses, or to provide a test function.

It will be appreciated that each of the disclosed devices for extending the useful lifetime of a primary battery power source may be incorporated individually or in various combinations in implantable cardiac pacers as desired.

While the invention has been particularly shown and described with reference to certain preferred embodiments thereof, it will be understood by those skilled in the art that various changes in form and detail may be made without departing from the spirit and scope of the invention.

What is claimed is:

1. A system for selectively powering a cardiac pacer implanted in a patient, which system comprises:
   electromagnetic energy transmitting means disposed externally of said patient for transmitting energy to said pacer and comprising:
   a large-diameter electromagnetic energy transmitting coil;
   furniture means for housing said large-diameter coil; and
   means for powering said large-diameter coil; pacer means in said pacer for producing a cardiac pacing electrical output;
   primary battery power means in said pacer for providing a voltage to power said pacing means;
   implantable means for detecting electromagnetic energy transmitted from said external energy transmitting means and comprising receiving coil means loosely coupled to said large-diameter coil for receiving electromagnetic energy therefrom;
   rectifying means, comprising a first semiconductor diode operatively connected between said energy receiving means and said pacing means, for providing a rectified D.C. voltage to said pacing means whenever sufficient energy is received by said receiving means to produce a rectified D.C. voltage of greater magnitude than the voltage provided to said pacing means by said primary battery power means; and
   unidirectional current conducting means, comprising a second semiconductor diode operatively connected between said primary battery power means and said pacing means, for conducting current between said primary battery power means and said pacing means to supply a D.C. voltage from said primary battery power means to said pacing means in the absence of a rectified D.C. voltage from said rectifying means, and for preventing the conduction of current between said pacing means and said primary battery power means in the presence of a rectified D.C. voltage provided from said rectifying means.

2. A system as in claim 1 further comprising:
   a third semiconductor diode in series with said energy receiving coil and said first semiconductor diode, and operatively connected to said energy receiving coil at a first junction and to said first semiconductor diode at a second junction, with like polarity to that of said first diode; and
   a secondary rechargeable battery power source of substantially lower energy capacity than said primary battery power source, operatively connected to said second junction and having a fully-charged voltage which exceeds the no-load voltage of said primary battery power source.

3. A system as in claim 2, further comprising means operatively connected to said first junction for limiting the output voltage of said energy receiving coil.

4. A system for extending the life of an implantable cardiac pacer of the type comprising:
   pacing means in said pacer for producing a cardiac pacing electrical output; and
   an internal primary battery power source having an initial output voltage higher than the operating voltage of said pacing means;

in which the improvement comprises:
a series-type voltage regulator means, connected between said primary battery power source and said pacing means, for constantly providing said operating voltage to said pacing means thus reducing the current drain from said primary battery power source while said output voltage is higher than said operating voltage.

5. A system as in claim 4 further comprising means for bypassing said voltage regulator means and means disposed externally of said implantable cardiac pacer for controlling said bypass means.

6. A system for selectively powering an implantable cardiac pacer, having an internal primary battery power source, from an external transmitting source, which system comprises:
pacing means in said pacer for producing a cardiac pacing electrical output;
implantable energy receiving means for detecting electromagnetic energy transmitted from said external energy source, which means comprises an electromagnetic energy receiving coil;
rectifying means comprising a first semiconductor diode operatively connected between said energy receiving means and said pacing means, for providing a rectified D.C. voltage to said pacing means whenever sufficient energy is received by said receiving means to produce a rectified D.C. voltage of greater magnitude than the voltage provided to said pacing means by said internal primary battery;
unidirectional current conducting means, comprising a series-type voltage regulator means for regulating the voltage applied to said pacer by said primary battery power source and operatively connected between said primary battery and said pacing means, for conducting current between said primary battery and said pacing means to supply a D.C. voltage from said primary battery to said pacing means in the absence of a rectified D.C. voltage from said rectifying means, and for preventing the conduction of current between said pacing means and said primary battery in the presence of a rectified D.C. voltage provided from said rectifying means;
a second semiconductor diode in series with said energy receiving coil and said first semiconductor diode and operatively connected to said energy receiving coil at a first junction and to said first semiconductor diode at a second junction with like polarity to that of said first diode; and
a secondary rechargeable battery power source, of substantially lower energy capacity than said primary battery power source, operatively connected to said second junction and having a fully charged voltage which exceeds the no-load voltage of said primary battery power source.

7. A system as in claim 6 further comprising means for bypassing said voltage regulator means and means disposed externally of said implantable cardiac pacer for controlling said bypass means.

* * * * *